(12) United States Patent
Hadba et al.

(10) Patent No.: US 8,790,488 B2
(45) Date of Patent: *Jul. 29, 2014

(54) BIOCOMPATIBLE SURGICAL COMPOSITIONS

(71) Applicant: Covidien LP, Mansfield, MA (US)

(72) Inventors: Ahmad R. Hadba, Fort Worth, TX (US); Nadya Belcheva, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/732,699

(22) Filed: Jan. 2, 2013

(65) Prior Publication Data
US 2013/0138148 A1 May 30, 2013

Related U.S. Application Data

(63) Continuation of application No. 11/636,159, filed on Dec. 8, 2006, now Pat. No. 8,449,714.

(60) Provisional application No. 60/748,395, filed on Dec. 8, 2005.

(51) Int. Cl.
| | | |
|---|---|---|
| *C09J 4/00* | (2006.01) | |
| *C08G 18/32* | (2006.01) | |
| *C08G 18/42* | (2006.01) | |
| *C09J 177/00* | (2006.01) | |
| *A61L 24/04* | (2006.01) | |
| *A61B 17/00* | (2006.01) | |
| *C08G 18/48* | (2006.01) | |
| *C08G 18/46* | (2006.01) | |
| *C09J 175/04* | (2006.01) | |
| *C08G 18/28* | (2006.01) | |
| *C08G 18/10* | (2006.01) | |

(52) U.S. Cl.
CPC ........... *C09J 177/00* (2013.01); *C08G 18/3278* (2013.01); *C08G 18/4277* (2013.01); *C08G 2230/00* (2013.01); *C08G 18/3281* (2013.01); *C08G 18/3206* (2013.01); *A61L 24/04* (2013.01); *A61B 17/0057* (2013.01); *C08G 18/4887* (2013.01); *C08G 18/4615* (2013.01); *C09J 175/04* (2013.01); *C08G 2190/00* (2013.01); *C08G 18/283* (2013.01); *C08G 18/10* (2013.01)
USPC ......... 156/331.7; 156/331.4; 528/44; 528/59; 528/61; 528/62; 528/64; 528/77; 528/85; 524/589; 524/590; 524/591

(58) Field of Classification Search
USPC ........................ 528/44, 59, 77, 85, 61, 62, 64; 156/331.4, 331.7; 524/589, 590, 591
See application file for complete search history.

(56) References Cited

U.S. PATENT DOCUMENTS

| | | |
|---|---|---|
| 3,631,138 A | 12/1971 | Peters |
| 3,773,595 A | 11/1973 | Burba et al. |
| 3,879,493 A | 4/1975 | Mudde |
| 3,903,232 A | 9/1975 | Wood et al. |
| 3,964,955 A | 6/1976 | Hirooka et al. |
| 3,976,550 A | 8/1976 | Cartmell et al. |
| 4,057,535 A | 11/1977 | Lipatova et al. |
| 4,061,662 A | 12/1977 | Marans et al. |
| 4,132,839 A | 1/1979 | Marans et al. |
| 4,169,175 A | 9/1979 | Marans et al. |
| 4,321,350 A | 3/1982 | Lehmann |
| 4,323,491 A | 4/1982 | Veselovsky et al. |
| 4,404,296 A | 9/1983 | Schapel |
| 4,425,472 A | 1/1984 | Howard et al. |
| 4,451,627 A | 5/1984 | Frisch, Jr. et al. |
| 4,477,604 A | 10/1984 | Oechsle, III |
| 4,511,626 A | 4/1985 | Schumacher |
| 4,547,561 A | 10/1985 | Wegner |
| 4,654,409 A | 3/1987 | Shirai et al. |
| 4,681,934 A | 7/1987 | Shibanai et al. |
| 4,722,815 A | 2/1988 | Shibanai |
| 4,740,534 A | 4/1988 | Matsuda et al. |
| 4,743,632 A | 5/1988 | Marinovic |
| 4,762,899 A | 8/1988 | Shikinami |
| 4,804,691 A | 2/1989 | English et al. |
| 4,806,614 A | 2/1989 | Matsuda et al. |
| 4,829,099 A | 5/1989 | Fuller et al. |
| 4,883,837 A | 11/1989 | Zabrocki |
| 4,914,173 A | 4/1990 | Ansell |
| 4,994,208 A | 2/1991 | McBain et al. |
| 4,994,542 A | 2/1991 | Matsuda et al. |

(Continued)

FOREIGN PATENT DOCUMENTS

| | | |
|---|---|---|
| EP | 0 077 192 A2 | 4/1983 |
| EP | 0 271 292 B1 | 6/1988 |

(Continued)

OTHER PUBLICATIONS

Margolin A L et al.: "Steroselective Oligomerizations Catalyzed by Lipases in Organic Olvents"; Tetrahedron Letters, vol. 28, No. 15, 1987pp. 1607-1610.

(Continued)

*Primary Examiner* — Michael L Leonard

(57) ABSTRACT

Biocompatible macromer compositions are provided including an isocyanate-functional polyalkylene oxide combined with at least one multi-functional isocyanate as a first component, and a multi-amino functional compound possessing multiple primary amines as a second component. The isocyanate-functional polyalkylene oxide has pendant polyalkylene oxide groups. The resulting biocompatible macromer composition can be employed as an adhesive or sealant for medical/surgical uses.

14 Claims, No Drawings

(56) References Cited

U.S. PATENT DOCUMENTS

| | | | |
|---|---|---|---|
| 4,997,656 A | 3/1991 | Shikinami et al. | |
| 5,017,625 A | 5/1991 | Ansell | |
| 5,065,752 A | 11/1991 | Sessions et al. | |
| 5,082,663 A | 1/1992 | Konishi et al. | |
| 5,087,686 A | 2/1992 | Ansell et al. | |
| 5,104,909 A | 4/1992 | Grasel et al. | |
| 5,166,300 A | 11/1992 | Rumon et al. | |
| 5,169,720 A | 12/1992 | Braatz et al. | |
| 5,173,301 A | 12/1992 | Itoh et al. | |
| 5,175,228 A | 12/1992 | Wang et al. | |
| 5,204,110 A | 4/1993 | Cartmell et al. | |
| 5,296,518 A | 3/1994 | Grasel et al. | |
| 5,346,981 A | 9/1994 | Sarpeshkar et al. | |
| 5,373,050 A | 12/1994 | Morikawa et al. | |
| 5,374,704 A | 12/1994 | Muller et al. | |
| 5,389,718 A | 2/1995 | Potter et al. | |
| 5,457,141 A | 10/1995 | Matsuda | |
| 5,462,536 A | 10/1995 | Braatz et al. | |
| 5,514,379 A | 5/1996 | Weissleder et al. | |
| 5,527,856 A | 6/1996 | Rhee et al. | |
| 5,574,104 A | 11/1996 | Kolycheck et al. | |
| 5,574,123 A | 11/1996 | Bock et al. | |
| 5,578,662 A | 11/1996 | Bennett et al. | |
| 5,603,798 A | 2/1997 | Bhat | |
| 5,631,341 A | 5/1997 | Morishima et al. | |
| 5,652,300 A | 7/1997 | Morikawa et al. | |
| 5,672,652 A | 9/1997 | Bhat | |
| 5,688,860 A | 11/1997 | Croft | |
| 5,703,158 A | 12/1997 | Duan et al. | |
| 5,717,030 A | 2/1998 | Dunn et al. | |
| 5,780,573 A | 7/1998 | Iwata et al. | |
| 5,791,352 A | 8/1998 | Reich et al. | |
| 5,795,633 A | 8/1998 | Yokoyama et al. | |
| 5,807,944 A | 9/1998 | Hirt et al. | |
| 5,869,566 A | 2/1999 | Thomas | |
| 5,874,500 A | 2/1999 | Rhee et al. | |
| 5,900,473 A | 5/1999 | Acevedo et al. | |
| 5,912,193 A | 6/1999 | Iwata et al. | |
| 5,922,809 A | 7/1999 | Bhat et al. | |
| 5,948,427 A | 9/1999 | Yamamoto et al. | |
| 5,976,305 A | 11/1999 | Bhat et al. | |
| 5,985,990 A | 11/1999 | Kantner et al. | |
| 5,990,237 A | 11/1999 | Bentley et al. | |
| 6,071,530 A | 6/2000 | Polson | |
| 6,103,850 A | 8/2000 | Reichel et al. | |
| 6,154,089 A | 11/2000 | Rombach | |
| 6,162,241 A | 12/2000 | Coury et al. | |
| 6,197,915 B1 | 3/2001 | Yamana et al. | |
| 6,207,751 B1 | 3/2001 | Nakabayashi et al. | |
| 6,211,249 B1 | 4/2001 | Cohn et al. | |
| 6,217,894 B1 | 4/2001 | Sawhney et al. | |
| 6,235,815 B1 | 5/2001 | Loercks et al. | |
| 6,261,544 B1 | 7/2001 | Coury et al. | |
| 6,290,729 B1 | 9/2001 | Sleplan et al. | |
| 6,296,908 B1 | 10/2001 | Reihs et al. | |
| 6,297,349 B1 | 10/2001 | Goldberg et al. | |
| 6,312,725 B1 | 11/2001 | Wallace et al. | |
| 6,352,710 B2 | 3/2002 | Sawhney et al. | |
| 6,395,112 B1 | 5/2002 | Sitzmann et al. | |
| 6,395,823 B1 | 5/2002 | Brink et al. | |
| 6,416,740 B1 | 7/2002 | Unger | |
| 6,458,889 B1 | 10/2002 | Trollas et al. | |
| 6,461,631 B1 | 10/2002 | Dunn et al. | |
| 6,465,001 B1 | 10/2002 | Hubbell et al. | |
| 6,465,004 B1 | 10/2002 | Rossi-Montero et al. | |
| 6,495,127 B1 | 12/2002 | Wallace et al. | |
| 6,512,033 B1 | 1/2003 | Wu | |
| 6,555,645 B1 | 4/2003 | Ikeda et al. | |
| 6,565,969 B1 | 5/2003 | Lamon et al. | |
| 6,566,406 B1 | 5/2003 | Pathak et al. | |
| 6,576,702 B2 | 6/2003 | Anderle et al. | |
| 6,579,952 B1 | 6/2003 | Niki et al. | |
| 6,582,713 B2 | 6/2003 | Newell et al. | |
| 6,605,666 B1 | 8/2003 | Scholz et al. | |
| 6,824,703 B2 | 11/2004 | Lawrey et al. | |
| 2001/0009662 A1 | 7/2001 | Cohn et al. | |
| 2001/0018072 A1 | 8/2001 | Unger | |
| 2002/0028875 A1 | 3/2002 | Anderle et al. | |
| 2002/0039594 A1 | 4/2002 | Unger | |
| 2003/0012734 A1 | 1/2003 | Pathak et al. | |
| 2003/0032734 A1 | 2/2003 | Roby | |
| 2003/0035786 A1 | 2/2003 | Hendriks et al. | |
| 2003/0044380 A1 | 3/2003 | Zhu et al. | |
| 2003/0089733 A1 | 5/2003 | Cain et al. | |
| 2003/0176615 A1 | 9/2003 | Lawrey et al. | |
| 2003/0195293 A1 | 10/2003 | Lubnin et al. | |
| 2003/0221687 A1 | 12/2003 | Kaigler | |
| 2004/0019178 A1 | 1/2004 | Gross et al. | |
| 2004/0023842 A1 | 2/2004 | Pathak et al. | |
| 2004/0068078 A1 | 4/2004 | Milbocker | |
| 2004/0092695 A1 | 5/2004 | Hu et al. | |
| 2004/0198901 A1 | 10/2004 | Graham et al. | |
| 2004/0198944 A1 | 10/2004 | Meltzer et al. | |
| 2004/0242831 A1 | 12/2004 | Tian et al. | |
| 2004/0259768 A1 | 12/2004 | Krebs | |
| 2005/0004661 A1 | 1/2005 | Lewis et al. | |
| 2005/0013793 A1* | 1/2005 | Beckman et al. | 424/78.27 |
| 2005/0069573 A1 | 3/2005 | Cohn et al. | |
| 2005/0070913 A1 | 3/2005 | Milbocker et al. | |
| 2005/0129733 A1 | 6/2005 | Milbocker et al. | |
| 2005/0131192 A1 | 6/2005 | Matsuda et al. | |
| 2005/0142162 A1 | 6/2005 | Hunter et al. | |
| 2005/0147647 A1 | 7/2005 | Glauser et al. | |
| 2005/0154148 A1 | 7/2005 | Nakamichi et al. | |
| 2005/0215748 A1 | 9/2005 | Milbocker | |
| 2005/0266086 A1 | 12/2005 | Sawhney | |
| 2007/0128152 A1 | 6/2007 | Hadba et al. | |
| 2007/0129505 A1 | 6/2007 | Hadba et al. | |
| 2007/0135605 A1 | 6/2007 | Hadba et al. | |
| 2007/0135606 A1 | 6/2007 | Belcheva et al. | |

FOREIGN PATENT DOCUMENTS

| | | |
|---|---|---|
| EP | 0 282 554 B1 | 9/1988 |
| EP | 0 301 516 B1 | 2/1989 |
| EP | 0 305 175 B1 | 3/1989 |
| EP | 0305175 A1 | 3/1989 |
| EP | 0 482 467 A2 | 4/1992 |
| EP | 0 488 629 A1 | 6/1992 |
| EP | 0 775 773 A1 | 5/1997 |
| EP | 1 391 205 A1 | 2/2005 |
| EP | 1 719 530 A | 11/2006 |
| EP | 1857489 A1 | 11/2007 |
| GB | 985 144 | 3/1965 |
| GB | 1 143 309 | 2/1969 |
| GB | 1 187 362 | 4/1970 |
| JP | 6263850 | 9/1994 |
| JP | 2002060341 | 2/2002 |
| WO | WO 88/01878 A1 | 3/1988 |
| WO | WO 99/02168 A1 | 1/1999 |
| WO | WO 99/14259 A1 | 3/1999 |
| WO | WO 99/30620 A1 | 6/1999 |
| WO | WO 00/06611 A1 | 2/2000 |
| WO | WO 00/33764 A1 | 6/2000 |
| WO | WO 00/43050 A1 | 7/2000 |
| WO | WO 01/00246 A | 1/2001 |
| WO | WO 01/06829 A2 | 2/2001 |
| WO | WO 01/16210 A | 3/2001 |
| WO | WO 02/40070 A2 | 5/2002 |
| WO | WO 02/056790 A2 | 7/2002 |
| WO | WO 02/074533 A2 | 9/2002 |
| WO | WO 02/076431 A1 | 10/2002 |
| WO | WO 02/100525 A2 | 12/2002 |
| WO | WO 03/011173 A2 | 2/2003 |
| WO | WO 03/011173 A3 | 2/2003 |
| WO | WO 03/027155 A1 | 4/2003 |
| WO | WO 03/040211 A2 | 5/2003 |
| WO | WO 03/040211 A3 | 5/2003 |
| WO | 03/049637 A2 | 6/2003 |
| WO | WO 2004/039323 A2 | 5/2004 |
| WO | WO 2004/039323 A3 | 5/2004 |
| WO | WO 2004/039857 A1 | 5/2004 |
| WO | WO 2004/041890 A1 | 5/2004 |
| WO | WO 2005/032461 A2 | 4/2005 |

(56) References Cited

FOREIGN PATENT DOCUMENTS

| WO | WO 2005/100429 A1 | 10/2005 |
|----|-------------------|---------|
| WO | WO 2006/010278 A1 | 2/2006 |
| WO | WO 2006/084911 A2 | 8/2006 |
| WO | WO 2006/107957 A2 | 10/2006 |
| WO | WO 2006/128742 A2 | 12/2006 |
| WO | WO 2006/128918 A1 | 12/2006 |
| WO | WO 2007/001448 A2 | 1/2007 |
| WO | 2007067621 A2 | 6/2007 |
| WO | WO 2007/067623 A | 6/2007 |
| WO | WO 2008/047100 A1 | 4/2008 |

OTHER PUBLICATIONS

Okumura S. et al.: "Synthesis of Ester Oligomer by AspergillNiger Lipase" Agricultural and Biological Chemistry, vol. 48, No. 11, 1984, pp. 2805-2808.

Lumann N R et al.: The convergent Synthesis of Poly(glycerol-succinine acid) Dendritic Marcomolecules: Chemistry—A European Journal, VCH Publishers, US vol. 9, 2003, pp. 5618-5626.

Database WPI, Section Ch, Week 199442 Derwent Publications Ltd. London, GB; Class A23, AN 1994-3383493.

Nivasu V M et al.: "In Situ Polymerizable Polyethyleneglycol Containing Polyesterpolyol Acrylates for Tissue Sealant Applications"; Biomaterials 2004 United Kingdom, vol. 25, No. 16, 2004, pp. 3283-3291.

Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.

M. J. Song, et al.: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.

Mei Xuan Xu et al.: Synthesis and Properties of Unsaturated Polyester Dio-Polyurethanehybrid Polymer Network: Journal of Applied Polymer Science, John Wiley and Sons Inc. New York, US , vol. 54, No. 11, Dec. 12, 1994, pp. 1659-1663.

Oprea S. et al.: "Poly(urethane-methacrylates)s. Synthesis and Characterization"; Polymer, Elsevier Science Publishers B.V., GB, vol. 42, No. 17, Aug. 2001, pp. 7257-7266.

Ferreira, et al., "Modification of the Biopolymer Castor Oil With Free Isocyanate Groups to Be Applied As Bioadhesive", *International Journal of Biological Macromolecules*, vol. 40, No. 2, pp. 144-152 (2007).

Ferreira, et al., "Development of a Biodegradable Bioadhesive Containing Urethane Groups", *Journal of Materials Science: Materials in Medicine*, vol. 19, No. 1, pp. 111-120 (2007).

European Search Report (EP 06 00 9170) dated Aug. 24, 2006.

International Search Report from Application EP 07 00 1213 dated Sep. 6, 2007.

International Search Report from Application EP 03 77 9244 dated Sep. 26, 2007.

International Search Report from Application PCT/US2006/46553 dated Oct. 31, 2007.

International Search Report from Application PCT/US2006/46554 dated Oct. 31, 2007.

International Search Report from PCT/US06/47013 dated Oct. 3, 2007.

International Search Report from PCT/US06/46558 dated Nov. 9, 2007.

International Search Report from PCT/US06/46552 dated Nov. 15, 2007.

International Search Report from PCT/US06/47023 dated Nov. 21, 2007.

International Search Report from PCT/US06/47013 dated Oct. 2, 2007.

International search Report (PCT/US06/47173 dated Oct. 2, 2007).

International Search Report from Application No. PCT/US08/60971 dated Jul. 18, 2008.

European Search Report for Appln. No. EP 08 25 1790.5 completed Jun. 19, 2009.

European Search Report for Appln. No. EP 08 25 3647 completed Mar. 6, 2009.

International Search Report from European Application No. EP 08 25 3645 mailed Mar. 5, 2009.

International Search Report from European Application No. EP 06 84 4894 date of completion Jun. 9, 2010.

International Search Report from European Application No. Ep 06 84 4890 date of completion Jun. 4, 2010.

Search Report dated Nov. 8, 2013 issued in European Appl. No. 10251822.2.

European Search Report for EP 06847553.2-2115 date of completion is Oct. 18, 2010 (6 pages).

\* cited by examiner

BIOCOMPATIBLE SURGICAL COMPOSITIONS

CROSS-REFERENCE TO RELATED APPLICATIONS

This application is a continuation of U.S. patent application Ser. No. 11/636,159, filed Dec. 8, 2006, now U.S. Pat. No. 8,449,714, which claims priority to, and the benefit of, U.S. Provisional Patent Application No. 60/748,395 filed Dec. 8, 2005, the entire disclosures of each of which are incorporated by reference herein.

TECHNICAL FIELD

The present disclosure relates to compositions useful as surgical adhesives or sealants. The compositions include a biocompatible macromer capable of forming a matrix, a multi-functional isocyanate compound and a compound possessing multiple primary amines.

DESCRIPTION OF THE RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed.

It would be desirable to provide a fully synthetic biological adhesive or sealant that is flexible, biocompatible and highly consistent in its properties.

SUMMARY

The present disclosure is directed to biocompatible macromer compositions which include an isocyanate-functional polyalkylene oxide in combination with at least one multifunctional isocyanate and a polyamino functional compound possessing multiple primary amines. The isocyanate-functional polyalkylene oxide may possess pendant polyalkylene oxide groups.

In embodiments, the isocyanate-functional polyalkylene oxide may be of the formula $$R-(NCO)_z$$

wherein, z is ≤1, and R is selected from the group consisting of polyalkylene oxides, polyethylene glycols with lactide linkages, and copolymers of polyethylene oxide with polypropylene oxide.

The biocompatible macromer compositions of the present disclosure may be utilized as adhesives or sealants in a variety of applications, including medical and/or surgical applications. In embodiments, the present disclosure includes methods for closing wounds by applying a biocompatible macromer composition of the present disclosure to a wound and allowing the biocompatible macromer composition to set, thereby closing said wound. Such wounds may include, in embodiments, incisions. Compositions of the present disclosure may also be utilized to fill voids in tissue. In embodiments, compositions of the present disclosure may be utilized to adhere a medical device, such as an implant, to a surface of animal tissue.

DETAILED DESCRIPTION

The present disclosure relates to compositions for use as a tissue adhesive or sealant, which are biocompatible, non-immunogenic and, in some embodiments, biodegradable. The compositions of the present disclosure include two components. The first component includes an isocyanate-functional polyalkylene oxide and, optionally, a multi-functional isocyanate compound. The second component includes a compound possessing multiple primary amines.

The isocyanate-functional polymer of the first component can be any biocompatible polyalkylene oxide-based polymer that contains an isocyanate functionality. The polymer can be a polyalkylene oxide (PAO) homopolymer or copolymer, or can be a block copolymer wherein at least one block is a polyalkylene oxide block. Suitable PAOs include polyethylene oxide ("PEO"), polypropylene oxide ("PPO"), polyethylene oxide-co-polypropylene oxide, polyethylene glycol ("PEG"), polypropylene glycol ("PPG"), and co-polyethylene oxide block or random copolymers. As used herein, polyethylene glycol generally refers to a polymer with a molecular weight of less than 50,000, while polyethylene oxide is used for higher molecular weights. PEGs provide excellent water retention, flexibility and viscosity in the biocompatible macromer composition.

PAOs can be functionalized to have multiple pendant groups according to any method known to those skilled in the art, including, for example, in Chapter 22 of Poly(ethylene Glycol) Chemistry: Biotechnical and Biomedical Applications, J. Milton Harris, ed., Plenum Press, NY (1992). Various forms of PAOs, in particular PEGs, are commercially available from providers which include, for example, Shearwater Polymers, Inc., Huntsville, Ala., and Texaco Chemical Company Houston, Tex.

In some embodiments the isocyanate-functional polymer can be a compound corresponding to the following formula (I):

$$R-(NCO)_z \qquad (I)$$

wherein z is ≤1, in embodiments from about 2 to about 8; and R is a polyalkylene oxide-based polymer, such as a polyethylene glycol with lactide linkages, or a poloxamer such as polyethylene oxide (PEO) copolymer with polypropylene oxide (PPO), including the triblock PEO-PPO copolymers commercially available as PLURONICS® from BASF Corporation (Mt. Olive, N.J.).

In embodiments, the isocyanate-functional polymer can be a compound corresponding to the following formula (II):

$$OCN-X-NCO-R-OCN-X-NCO \quad (II)$$

where R is as defined above and X is an aliphatic or aromatic group.

In some embodiments, the isocyanate-functional polymer of the first component can include hydrolytically degradable bonds, so that the isocyanate-functional polymer becomes biodegradable. Hydrolytically degradable bonds can be incorporated into the isocyanate-functional polymer by forming the polymer using monomers that include, but are not limited to, hydrolytically labile α-hydroxy acids such as lactic acid, glycolic acid, lactide and glycolide lactones including ε-caprolactone, carbonates such as trimethylene carbonate, ester ethers such as dioxanones, diacids including azelaic acid, succinnic acid, adipic acid, sebacic acid, malonic acid, glutaric acid, and the like, phosphoesters such as ethyl dichlorophosphate, anhydrides including azelaic acid anhydride and sebacic acid anhydride, and combinations thereof.

Hydrolytically degradable bonds can be incorporated into the isocyanate-functional polymer, for example, by reacting a polyalkylene oxide-based polymer and one or more of the afore-mentioned monomers with small amounts of diol. A low molecular weight PEG polymer can advantageously be used as part of the diol mixture. The selected diol is chosen to provide desired properties to the final product. For example, where mechanical enhancement is not desired or necessary, diethylene glycol or a short chain PEG diol can be used as the diol. Where additional strength of the sealant is desired, phthalic, biphenyl, bisphenol A, or diglycidyl ether of bisphenol A groups can be used as the diol.

In other embodiments, degradable linkages may be incorporated into the isocyanate-functional polyalkylene oxide by reacting the polyalkylene oxide with a polyhydric alcohol such as D-sorbitol, D-mannitol, sucrose, dextrose, tris(hydroxymethyl)aminomethane (also known as 2-amino-2-(hydroxymethyl)-1,3-propanediol), enterodiol, pentaerythritol, cyclodextrins, and the like to form a polyalkylene oxide having multiple hydroxy groups. The following formula III is illustrative of polyalkylene oxide compounds having multiple hydroxy groups:

$$R-(OH)_w \quad (III)$$

where R is as defined above and w is a number from about 2 to about 20.

The polyalkylene oxide having multiple hydroxy groups may then, in turn, be reacted with a compound capable of forming degradable groups including hydroxy acids such as lactic acid or glycolic acid, lactide, glycolide, lactones such as ε-caprolactone, carbonates such as trimethylene carbonate, ester ethers such as dioxanones including 1,4-dioxane-2-one and 1,3-dioxane-2-one, to form a polyalkylene oxide having groups such as polyglycolic acid (PGA), polylactic acid (PLA), polycaprotactone (PCL), polydioxanone (PDO), polytrimethylene carbonate (PTMC), and the like or combinations thereof. Thus, the resulting formula can be $$R-(R_1-OH)_d \quad (IV)$$

where R is as defined above, $R_1$ is a degradable group, and d is a number from 2 to 20.

This polyalkylene oxide having multiple degradable groups/hydroxy groups may, in turn, be reacted with a diisocyanate to produce isocyanate-functional polyalkylene oxide having degradable linkages of formula $$R-[R_1-OCN-X-NCO]_d \quad (V)$$

wherein R, $R_1$, X and d are as defined above.

Where present, components providing degradable linkages can be present in the isocyanate-functional polyalkylene oxide in amounts from about 5% to about 50% by weight of the isocyanate-functional polyalkylene oxide, in embodiments from about 7% to about 40% by weight of the isocyanate-functional polyalkylene oxide, typically from about 10% to about 30% by weight of the isocyanate-functional polyalkylene oxide.

In addition to, or in place of, components that provide hydrolytically degradable linkages, at least one linkage that is enzymatically degradable may be incorporated into the isocyanate-functional polyalkylene oxide so that it becomes biodegradable. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln(Arg)$_2$-, Phe-Arg-, -(Ala)$_3$-, -(Ala)$_2$-, -Ala -Ala (D)-, -(Ala)$_2$-Pro-Val-, -(Val)$_2$-, -(Ala)$_2$-Leu-, -Gly-Leu-, -Phe-Leu-, -Val-Leu-Lys-, -Gly -Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$-, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the isocyanate-functional polyalkylene oxide.

The isocyanate-functional polyalkylene oxide can have a branched or star configuration for improved biodegradability. The molecular weight of the isocyanate-functional polyalkylene oxide can be from about 500 to about 100,000, in embodiments from about 750 to about 20,000, typically from about 1000 to about 10,000.

Methods for producing the isocyanate-functional polymer are within the purview of those skilled in the art. For example, PAOs can be functionalized to have multiple pendant groups according to methods including, for example, those disclosed in Chapter 22 of Poly(ethylene Glycol) Chemistry: Biotechnical and Biomedical Applications, J. Milton Harris, ed., Plenum Press, NY (1992). Various forms of PAOs, in particular PEGs, are commercially available from providers which include, for example, Shearwater Polymers, Inc., Huntsville, Ala., and Texaco Chemical Company Houston, Tex.

In some embodiments the PAO may be a PEG which includes a pendant alkoxy group such as methoxy, i.e., it may be a methoxy PEG ("mPEG"). Specific examples of the isocyanate-functional polyalkylene oxide include methoxy-PEG isocyanate having the following formula

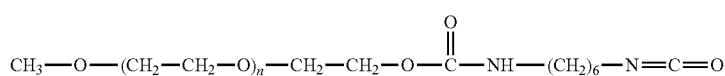

(VI)

where n is a number from 10 to 250, and methoxy-PEG triisocyanate having the following formula

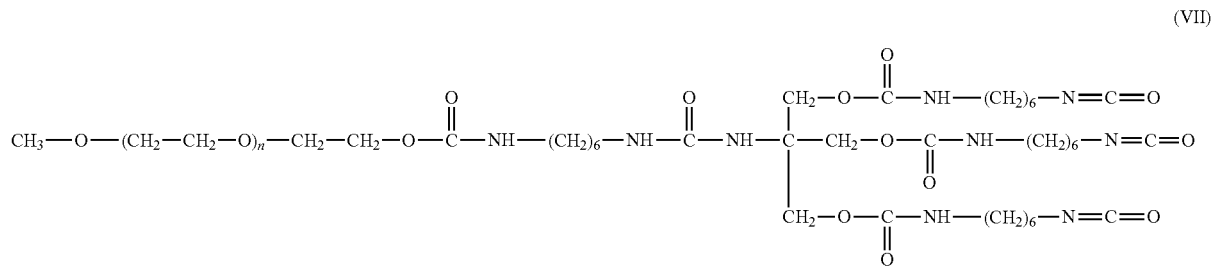

(VII)

Selection of the pendant polyalkylene oxide moieties of the isocyanate-functional polyalkylene oxide provides control of the hydrophilicity of the biocompatible macromer composition and the degree to which it will swell in situ, without sacrificing any physical or mechanical properties. Moreover, where desired, the hydrophilicity of the pendant polyalkylene oxide moiety can be utilized to reduce cell adhesion and protein deposition with the biocompatible macromer composition of the present disclosure.

The remainder of the first component of the biocompatible macromer composition of the present disclosure includes at least one multi-functional isocyanate such as diisocyanates, triisocyanates and combinations thereof. The additional multi-functional isocyanate may be in monomeric or polymeric form.

Suitable diisocyanates which may be utilized in the first component of the biocompatible macromer composition of the present disclosure include, but are not limited to, aromatic diisocyanates such as toluene diisocyanate, xylylene diisocyanate, bisphenylene diisocyanate, naphthylene diisocyanate, 4,4'-oxybis(phenyl isocyanate), 2,4,6-trimethyl-1,3-phenylene diisocyanate, and diphenylmethane diisocyanate; and acyclic aliphatic diisocyanates such as trimethylene diisocyanate, tetramethylene diisocyanate, pentamethylene diisocyanate, hexamethylene diisocyanate, ethylethylene diisocyanate, trimethylhexane diisocyanate, and heptanemethylene diisocyanate. Other diisocyanates which may be utilized include lysine diisocyanate, butane diisocyanate, and any combination of the foregoing diisocyanates.

Suitable triisocyanates which may be utilized include, but are not limited to, aromatic monomer triisocyanates such as triphenylmethane triisocyanate and tris(isocyanatophenyl)thiophosphate; aliphatic monomer triisocyanates such as lysine ester triisocyanate, 1,6,11-undecane triisocyanate, 1,3,6-hexamethylene triisocyanate and 1,8-diisocyanato-4-isocyanatomethyloctane; and alicyclic monomer triisocyanates such as bicycloheptane triisocyanate, as well as any combinations of the foregoing triisocyanates.

In other embodiments, suitable triisocyanates may be obtained by reacting a compound containing, in embodiments, three active hydrogen atoms with one of the diisocyanates described above. Compounds that contain three active hydrogen atoms include, for example, polyamines such as diethylene triamine, bis(hexamethylene) triamine, polypropylene oxide-based triamine, JEFFAMINE® T-403 and T-3000 (from Huntsman Performance Chemicals, Houston, Tex.), 2,4,6-triaminopyrimidine or 4,5,6-triaminopyrimidine, polyols, such as trimethyloyl propane, glycerol, imine triols, cyanuric acid. In one embodiment, adducts of diisocyanates and low molecular weight triols, more particularly the adducts of aromatic diisocyanates and triols, for example trimethyol propane or glycerol, are utilized as triisocyanates.

The isocyanate-functional polyalkylene oxide combined with the multi-isocyanate functional monomers and/or polymers are combined by methods known to those skilled in the art, including mixing, blending, etc., to form the first component of the biocompatible macromer composition of the present disclosure.

The ratio of isocyanate-functional polyalkylene oxide to multi-functional isocyanates in the first component can be from about 1:99 to about 99:1, in embodiments from about 2:98 to about 75:25, typically from about 5:95 to about 25:75.

The first component, i.e., the combination of isocyanate-functional polyalkylene oxide and multi-functional isocyanates, may be present in the biocompatible macromer composition of the present disclosure in amounts from about 50% to about 99% by weight of the biocompatible macromer composition, in embodiments from about 55% to about 95% by weight of the biocompatible macromer composition, typically from about 60% to about 90% by weight of the biocompatible macromer composition.

The second component of the biocompatible macromer composition of the present disclosure is a multi-amino functional compound possessing multiple primary amines. In one embodiment, the second component is monomeric. Suitable primary amines which may be utilized as the second component include polyamino functional compounds. Such compounds include, but are not limited to, ethylene diamine, hexamethylene diamine, lysine, spermidine (N-(3-aminopropyl)-1,4-butanediamine), spermine (N,N'-bis(3-aminopropyl)-1,4-butanediamine), isomers of hexamethylene diamine, diethylene triamine, triethylene tetramine, tetraethylene pentamine, bishexamethylene triamine, N,N'-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, and phenalkylene polyamines.

In another embodiment, the second component may be a polyamino functional macromer compound, including polyoxyalkylene amines sold under the name JEFFAMINE® by Huntsman Performance Chemicals (Houston, Tex.), other amino-functionalized polyalkylene oxides, polypeptides including polypeptides having lysine and/or arginine residues, and the like.

The second component may be present in the biocompatible macromer composition of the present disclosure in amounts from about 1% to about 50% by weight of the biocompatible macromer composition, in embodiments from about 5% to about 45% by weight of the biocompatible macromer composition, typically from about 10% to about 40% by weight of the biocompatible macromer composition.

The two components cross-link in situ when mixed together to form a biocompatible adhesive or sealant. This biocompatible macromer composition rapidly forms a three dimensional gel-like adhesive matrix, which reduces total surgical/operating time during a medical procedure. The biocompatible macromer composition can also act as a drug carrier, allowing controlled release and direct delivery of a drug to a specific location in an animal, especially a human. Each component may be synthetic to reduce or eliminate immuno-reactions in a subject's tissue.

Where degradable linkages are included in the isocyanate-functional polymer of the first component, the biocompatible macromer composition of the present disclosure is biodegradable.

This resulting biocompatible macromer composition can be used in a medical/surgical capacity in place of, or in combination with, sutures, staples, clamps and the like. In one embodiment, the biocompatible macromer composition can be used to seal or adhere delicate tissue together, such as lung tissue, in place of conventional tools that may cause mechanical stress. The resulting biocompatible macromer composition can also be used to seal air and/or fluid leaks in tissue as well as to prevent post-surgical adhesions and to fill voids and/or defects in tissue.

To prepare the biocompatible macromer composition, the first polymer is combined with the second component to form a three-dimensional crosslinked matrix as a result of the reaction between the functional groups on the first polymer with the amine groups on the second component.

The concentrations of the first polymer and the second component will vary depending upon a number of factors, including the types and molecular weights of the particular polymers used and the desired end use application, i.e., an adhesive or sealant.

The use of higher concentrations of both the first and second components will result in the formation of a more tightly crosslinked biocompatible macromer composition, producing a stiffer and stronger gel matrix. As such, biocompatible macromer compositions of the present disclosure intended for use in tissue augmentation will generally use higher concentrations of both the first and second components. Biocompatible macromer compositions of the present disclosure intended for use as bioadhesives or for the prevention of post-surgical adhesions need not be as firm and may therefore contain lower concentrations of the two components.

Biologically active agents may be included in the compositions of the present disclosure. For example, naturally occurring polymers, including proteins such as collagen and derivatives of various naturally occurring polysaccharides such as glycosaminoglycans, can be incorporated into the composition of the present disclosure. When these other biologically active agents also contain functional groups, the groups will react with the functional groups on the first and/or second components of the biocompatible macromer composition of the present disclosure.

A variety of optional ingredients including medicinal agents may also be added to the biocompatible macromer composition of the present disclosure. A phospholipid surfactant that provides antibacterial stabilizing properties and helps disperse other materials in the biocompatible macromer composition may be added to the composition of the present disclosure. Additional medicinal agents include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents.

Imaging agents such as iodine or barium sulfate, or fluorine, can also be combined with the composition of the present disclosure to allow visualization of the surgical area through the use of imaging equipment, including X-ray, MRI, and CAT scan.

Additionally, an enzyme may be added to the composition of the present disclosure to increase its rate of degradation. Suitable enzymes include, for example, peptide hydrolases such as elastase, cathepsin G, cathepsin E, cathepsin B, cathepsin H, cathepsin L, trypsin, pepsin, chymotrypsin, γ-glutamyltransferase (γ-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the biocompatible macromer composition of the present disclosure. Methods for incorporating enzymes into liposomes and/or microspheres are known to those skilled in the art.

The biocompatible macromer composition of the present disclosure can be used for a number of different human and animal medical applications including, but not limited to, wound closure (including surgical incisions and other wounds), adhesives for medical devices (including implants), sealants and void fillers, and embolic agents. These adhesives may be used to bind tissue together either as a replacement of, or as a supplement to, sutures, staples, tapes and/or bandages. Use of the disclosed adhesive can eliminate or substantially reduce the number of sutures normally required during current practices, and eliminate the subsequent need for removal of staples and certain types of sutures and thus can be particularly useful for use with delicate tissues where sutures, clamps or other conventional tissue closure mechanisms may cause further tissue damage.

Additional applications include sealing tissues to prevent or control blood, or other fluid leaks, at suture or staple lines. In another embodiment, the biocompatible macromer composition can be used to attach skin grafts and position tissue flaps during reconstructive surgery. In still another embodiment, the adhesive can be used to close tissue flaps in periodontal surgery.

The macromer composition can be dispensed from a conventional adhesive dispenser, which typically provides mixing of the first and second components prior to the dispenser. Such dispensers are disclosed, for example, in U.S. Pat. Nos. 4,978,336, 4,361,055, 4,979,942, 4,359,049, 4,874,368, 5,368,563, and 6,527,749, the disclosures of which are incorporated herein by reference.

In other embodiments, especially where the macromer composition of the present disclosure is to be utilized as a void filler or sealant to fill a defect in an animal's body, it may be advantageous to more precisely control the conditions and extent of cross-linking; in such a case, it may be desirable to partially cross-link the composition prior to its use to fill a void in animal tissue. In such a case the composition of the present disclosure is applied to the void or defect and allowed to set, thereby filling the void or defect.

To effectuate the joining of two tissue edges, the two edges are approximated, and the first component, i.e., the isocyanate-functional polyalkylene oxide combined with at least one multi-functional isocyanate, is combined with the second component, i.e., a monomeric compound possessing multiple primary amines. The two components crosslink rapidly, generally taking less than one minute. The composition of the present disclosure can be used as an adhesive to close a wound, including a surgical incision. In such a case, the composition of the present disclosure can be applied to the wound and allowed to set, thereby closing the wound.

While certain distinctions may be drawn between the usage of the terms "flesh" and "tissue" within the scientific community, the terms are used interchangeably herein as referring to a general substrate upon which those skilled in the art would understand the present adhesive to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic or ascite tissue.

In another embodiment, the present disclosure is directed to a method for using the biocompatible macromer composition of the present disclosure to adhere a medical device to tissue, rather than secure two edges of tissue. In some embodiments, depending on the composition of the medical device, a coating may be required on the medical device. In some cases such a coating can include the first component of the biocompatible macromer composition of the present disclosure, or the second component. In some aspects, the medical device includes an implant. Other medical devices include, but are not limited to, pacemakers, stents, shunts and the like. Generally, for adhering a device to the surface of animal tissue, the composition of the present disclosure can be applied to the device, the tissue surface or both. The device, biocompatible macromer composition and tissue surface are then brought into contact with each other and the composition is allowed to set, thereby adhering the device and surface to each other.

The present adhesive can also be used to prevent post surgical adhesions. In such an application, the biocompatible macromer composition is applied and cured as a layer on surfaces of internal tissues in order to prevent the formation of adhesions at a surgical site during the healing process.

In addition to the formation of adhesion barriers, in embodiments the biocompatible macromer compositions may be utilized to form implants such as gaskets, buttresses, or pledgets for implantation.

When used as a sealant, the composition of the present disclosure can be used in surgery to prevent or inhibit bleeding or fluid leakage both during and after a surgical procedure. It can also be applied to prevent air leaks associated with pulmonary surgery. The sealant may be applied directly to the desired area in at least an amount necessary to seal off any defect in the tissue and seal off any fluid or air movement.

Application of the adhesive or sealant, with or without other additives, can be done by any conventional means. These include dripping, brushing, or other direct manipulation of the adhesive on the tissue surface, or spraying of the adhesive to the surface. In open surgery, application by hand, forceps or the like is contemplated. In endoscopic surgery, the adhesive can be delivered through the cannula of a trocar, and spread at the site by any device known in the art.

The present biocompatible macromer composition has a number of advantageous properties. The resulting biocompatible macromer compositions of the present disclosure are safe and biocompatible, possess enhanced adherence to tissue, are biodegradable, have hemostatic potential, have low cost, and are easy to prepare and use. By varying the selection of the polymer components, the strength and elasticity of the biocompatible macromer composition can be controlled, as can the gelation time.

The biocompatible macromer composition rapidly forms a compliant gel matrix, which insures stationary positioning of tissue edges or implanted medical devices in the desired location and lowers overall required surgical/application time. The biocompatible macromer composition exhibits little or no swelling upon gel matrix formation, and therefore retains the positional integrity of the aligned tissue edges and/or location of a medical device. The biocompatible macromer composition forms strong cohesive bonds, based in part on a low percent of water content as compared to other adhesives. It exhibits excellent mechanical performance and strength, while retaining the necessary pliability to adhere living tissue. This strength and pliability allows a degree of movement of tissue without shifting the surgical tissue edge. Additionally, the biocompatible macromer composition is biodegradable, allowing the degradation components to pass safely through the subject's body.

In order that those skilled in the art may be better able to practice the present disclosure described herein, the following examples are provided to illustrate, but not limit, the features of the present disclosure.

Example 1

Activation of methoxy-PEGs. HMDI was added to a 100 mL chloroform solution of mPEG (Mw=2000) and triethylamine. The reaction mixture was heated to reflux and allowed to react overnight. The reaction product was concentrated on a ROTAVAPOR® rotary evaporator, (BÜCHI Labortechnik AG), then collected by precipitation in ether. The product was redissolved in chloroform and reprecipitated in ether, after which it was dried under vacuum. The compounds utilized were as follows:

TABLE 1

| Compound | MW | mMols | Weight (g) | Mol Ratio |
| --- | --- | --- | --- | --- |
| mPEG 2000 (Aldrich, Cat. # 20, 250-9) | 2000 | 0.01 | 20 | 1 |

TABLE 1-continued

| Compound | MW | mMols | Weight (g) | Mol Ratio |
|---|---|---|---|---|
| HMDI (Fluka Lot # 10317/1-40, 800) (b.p. 255° C.) | 168.2 | 0.1 | 16.8 | 10 |
| Triethylamine (Aldrich Batch # 06615BA d = 0.726 g/ml) | 101.19 | 0.03 | 3.03 | 3 |

Example 2

HMDI was added to mPEG (Mw=1900) and triethylamine following the procedures set forth above in Example 1. The reaction mixture was heated to reflux and allowed to react overnight. The reaction product was concentrated on a ROTAVAPOR® rotary evaporator, then collected by precipitation in ether. The product was redissolved in chloroform and reprecipitated in ether, after which it was dried under vacuum. The compounds utilized were as follows:

TABLE 2

| Compound | MW | mMols | Weight (g) | Mol Ratio |
|---|---|---|---|---|
| mPEG 2000 (Alfa Aesar, Lot # B12L29 Stock # 41563) | 1900 | 0.1 | 100 | 1 |
| HMDI (Fluka Lot # 10317/1-40, 800) (b.p. 255° C.) | 168 | 0.3 | 50.4 | 3 |
| Triethylamine (Aldrich Batch # 06615BA d = 0.726 g/ml) | 101 | 0.3 | 30 | 3 |

Example 3

Activation of mPEG-OH with HMDI. A methoxy-PEG having a molecular weight of 5000 was modified with HMDI following the procedures set forth above in Example 1. HMDI was added to mPEG 5000-OH in chloroform with triethylamine as a catalyst. The reaction proceeded under reflux for three days at which time the product was isolated by precipitation in PE/ether followed by drying under nitrogen gas. The yield was >80% as confirmed by Fourier transform infrared (FTIR), and nuclear magnetic resonance (NMR). The compounds utilized were as follows:

TABLE 3

| Compound | MW | mMols | Weight (g) | Mol Ratio |
|---|---|---|---|---|
| mPEG 5000-OH (Aldrich, Cat. # 20251-7) | 5000 | 0.001 | 5 | 1 |
| HMDI (Fluka Lot # 10317/1-40800) (b.p. 255° C.) | 168 | 0.010 | 1.68 | 10 |
| Triethylamine (Aldrich Batch # 06615BA d = 0.726 g/ml) | 101.19 | 0.003 | 0.3 | 3 |

Example 4

Condensation of functionalized mPEG with tris(hydroxymethyl)amino methane (THMAM). THMAM dissolved in N,N-Dimethyformamide (DMF) was heated to about 60-65° C. and added to a solution of mPEG-OCONH($CH_2$)$_6$NCO in chloroform. The mixture was combined for four hours. After concentrating the reaction mixture on a ROTAVAPOR® rotary evaporator, precipitation in ether followed. Final products were dried overnight under nitrogen. Yield was 70-80%. Analysis was by FTIR and NMR. The compounds utilized were as follows:

TABLE 4

| Compound | MW | mMols | Weight (g) | Mol Ratio |
|---|---|---|---|---|
| mPEG 2000-OCONH—($CH_2$)$_6$NCO | ~2180 | 2.3 | 5 | 1 |
| THMAM m.p. 171-172° C. (Alfa Aesar, Stock #31801 Lot #109M04) | 121.14 | 2.3 | 0.28 | 1 |

Example 5

Condensation of mPEG 5000-NCO with THMAM. The reaction scheme of Example 4 was followed. THMAM was dissolved in 1.5 mL of DMF with slight heating. mPEG 5000-NCO was heated to melting (~60-65° C.). The solution of THMAM in DMF was added drop-wise to the mPEG-5000-NCO melt. After the reaction was complete, 4 hours, ~50 mL of chloroform was added and the product was precipitated in ether. The product was then vacuum dried. Yield was ~80%. Analysis was by FTIR and NMR. The compounds utilized were as follows:

TABLE 5

| Compound | MW | mMols | Weight (g) | Mol Ratio |
|---|---|---|---|---|
| mPEG 5000-OCONH—($CH_2$)$_6$NCO | ~5170 | 0.77 | 4 | 1 |
| THMAM | 121 | 0.77 | 0.094 | 1 |

Example 6

Ring opening polymerization (ROP) of L-lactide. mPEG-HMDI-THMAM-(OH$_3$) and L-lactide were heated to about 110-115° C. Stannous octoate (Sn(Oct)$_2$) catalyst dissolved in toluene was added to the melt. The reaction time was 24 hours. The reaction mixture was dissolved in chloroform and precipitated in PE/ether. Final product was dried under vacuum under nitrogen. Analysis was by NMR and FTIR. Yield was >90%. The compounds utilized were as follows:

TABLE 6

| Compound | MW | mMols | Weight (g) | Mol Ratio |
|---|---|---|---|---|
| Lactide | 144 | 4.25 | 0.612 | 15 |
| mPEG 5000-HMDI-THMAM-(OH)$_3$ | ~5290 | 0.2835 | 1.5 | 1 |
| Sn (Oct)$_2$ | 405 | | 1.5-1.7 mg | 500-700 ppm |

Example 7

Functionalization of mPEG 5000-(L-lactide)$_3$-OH with HMDI. mPEG 5000-(L-lactide)$_3$-OH and triethylamine (catalyst) were dissolved in chloroform. This solution was gradually added to HMDI dissolved in chloroform and heated to 60-65° C. with stirring and refluxing under nitrogen. The reaction time was 4 hours. After reduction of solvent by a ROTAVAPOR® rotary evaporator, precipitation in PE/ether followed. Products were dried under vacuum under nitrogen. Yields >90%. Analysis was by NMR and FTIR. The compounds utilized were as follows:

TABLE 7

| Compound | MW | mMols | Weight (g) | Mol Ratio |
| --- | --- | --- | --- | --- |
| mPEG 5000-(L-lactide)$_3$-OH | 9611 | 0.416 | 4 | 1 |
| HMDI (Fluka Lot # 10317/1-40800) (b.p. 255° C.) | 168 | 10 | 1.68 | 24 |
| Triethylamine (Aldrich Batch # 06615BA d = 0.726 g/ml) | 101 | 2.31 | 0.231 | 3 |

Example 8

Condensation of mPEG 2000-HMDI with sorbitol. D-sorbitol was dissolved in DMF and triethylamine with slight heating. This solution was added drop-wise to a solution of mPEG 2000-NCO in chloroform. A slight precipitate formed. The mixture was heated and additional DMF added in 1mL increments until the ratio of DMF to chloroform was 1:2, and the total volume was ~30mL. The reaction proceeded for 12 hours at a temperature of 60-65° C. After reduction of the solvent by a ROTAVAPOR® rotary evaporator, precipitation in PE/ether (at a 1:1 ratio) followed. The yield was ~90% and confirmed by FTIR and NMR. The compounds utilized were as follows:

TABLE 8

| Compound | MW | mMols | Weight (g) | Mol Ratio |
| --- | --- | --- | --- | --- |
| mPEG 2000-NCO | 2291 | 1.3 | 3 | 1 |
| D-sorbitol (Alfa Aesar Lot # K 8m31, Stock # 36404 | 182 | 1.3 | 0.24 | 1 |
| Triethylamine d = 0.726 g/mL | 101 | 3.9 | 0.4 | 3 |

Example 9

ROP of L-lactide with mPEG 20000-sorbitol. mPEG 2000-HMDI-D-sorbitol and L-lactide were heated to 135-140° C. Sn(Oct)$_2$ catalyst was dissolved in toluene and added to the melt and the reaction was allowed to proceed overnight. The reaction mixture was dissolved in chloroform and precipitated in PE/ether (at a 1:1 ratio), and then re-dissolved and re-precipitated. Yield was >95%. Analysis was by NMR and FTIR. The compounds utilized were as follows:

TABLE 9

| Compound | MW | mMols | Weight (g) | Mol Ratio |
| --- | --- | --- | --- | --- |
| mPEG 2000-HMDI-D-sorbitol | 2473 | 1 | 2.5 | 1 |
| L-lactide | 144 | 50 | 7.2 | 50 |
| Sn(Oct)$_2$ | 405 | | 7 mg | 500-700 ppm |

Example 10

Functionalization of mPEG 2000-HMDI-sorbitol-(lactide-OH)$_5$ with HMDI. mPEG 2000-HMDI-sorbitol-(lactide-OH)$_5$ and triethylamine were dissolved in chloroform at room temperature. This solution was added to HMDI dissolved in chloroform with stirring. The reaction proceeded under reflux for 6 hours at 60-65° C. Product was precipitated in ether as a viscous sticky wax. Mixture was heated at ~20° C. for four hours. Product was re-dissolved in chloroform, and the solvent was removed by a ROTAVAPOR® rotary evaporator. Yield was ~85%. Analysis was by FTIR and NMR. The compounds utilized were as follows:

TABLE 10

| Compound | MW | mMols | Weight (g) | Mol Ratio |
| --- | --- | --- | --- | --- |
| mPEG 2000-HMDI-sorbitol-(lactide-OH)$_5$ | 9673 | 0.45 | 4.4 | 1 |
| HMDI (Fluka Lot # 10317/1-40800) (b.p. 255° C.) | 168 | 11.25 | 1.89 | 25 |
| Triethylamine (Aldrich Batch # 06615BA d = 0.726 g/ml) | 101 | 1.35 | ~0.2 (mL) | 3 |

Example 11

ROP of lactide using mPEG-HMDI-THMAM. mPEG 5000-HMDI-THMAM and L-lactide were heated to 135-140° C. under nitrogen. Sn(Oct)$_2$ was dissolved in toluene and added to the melt. The reaction was allowed to proceed for 24 hours. The reaction mixture was dissolved in chloroform, precipitated two times with ether, and dried using a ROTAVAPOR® rotary evaporator. Yield was ~35% and confirmed by NMR and FTIR.

Example 12

Functionalization to provide mPEG 2000-sorbitol(lactide-OH)$_5$ HMDI. This example followed the same procedure as Example 10. The compounds utilized were as follows:

TABLE 11

| Compound | MW | mMols | Weight (g) | Mol Ratio |
| --- | --- | --- | --- | --- |
| mPEG 2000 sorbitol-(lactide-OH)$_5$ | 9673 | 0.01 | 97 | 1 |
| HMDI (Fluka Lot # 10317/1-40800) (b.p. 255° C.) | 168 | 0.25 | 42 | 25 |

TABLE 11-continued

| Compound | MW | mMols | Weight (g) | Mol Ratio |
|---|---|---|---|---|
| Triethylamine (Aldrich Batch # 06615BA d = 0.726 g/ml) | 101 | 0.15 | 15 | 15 |

Solvent was chloroform, reaction time was 6 hours under reflux. NMR and FTIR confirmed results.

Example 13

Polycaprolactone diol (PCL diol) was combined with HMDI and triethylamine in THF solvent (~100 mL) and refluxed at 64° C. for four hours. The components utilized were as follows:

TABLE 12

| Compound | MW | mMols | Weight (g) | Mol Ratio |
|---|---|---|---|---|
| PCL diol | ~530 | 0.02 | 10.6 | 1 |
| HMDI | 168 | 0.044 | 7.4 | 2.2 |
| Triethylamine (Aldrich Batch # 06615BA d = 0.726 g/ml) | 101 | 0.005 | 0.5 | 0.25 |

After cooling down, PEG 200 and HMDI were added in THF. The reaction proceeded for four hours. The components utilized were as follows:

TABLE 13

| Compound | MW | mMols | Weight (g) | Mol Ratio |
|---|---|---|---|---|
| PEG 200 | 200 | 0.04 | 8 | 2 |
| HMDI | 168 | 0.044 | 7.4 | 2.2 |

The volume of the reaction mixture was reduced using a ROTAVAPOR® rotary evaporator and precipitated in ether. The product was re-dissolved in chloroform, which was then evaporated leaving a waxy white solid. Yield was ~95%.

Example 14

Polycaprolactone triol (PCL triol) was combined with HMDI in the presence of a triethylamine catalyst. The mixture was heated to ~64° C. for four hours under refluxing. The amounts of the components were as follows:

TABLE 14

| Compound | MW | mMols | Weight (g) | Mol Ratio |
|---|---|---|---|---|
| PCL triol | ~300 | 0.02 | 6 | 1 |
| HMDI | 168 | 0.062 | 10.4 | 3.1 |
| Triethylamine | 107 | 0.005 | 0.5 | 0.25 |

After cooling down, PEG 200 and HMDI were added as follows:

TABLE 15

| Compound | MW | mMols | Weight (g) | Mol Ratio |
|---|---|---|---|---|
| PEG 200 | 200 | 0.06 | 12 | 3 |
| HMDI | 168 | 0.062 | 10.4 | 3.1 |

The mixture was stirred and the reaction proceeded for four hours. Reduction of the volume was carried out on a ROTAVAPOR® rotary evaporator. Precipitation in ether produced a viscous oil. Yield was ~90%. Analysis by NMR and FTIR.

It will be understood that various modifications may be made to the embodiments disclosed herein. Therefore the above description should not be construed as limiting, but merely as exemplifications of useful embodiments. Those skilled in the art will envision other modifications within the scope and spirit of the claims appended hereto.

What is claimed is:

1. A biocompatible surgical adhesive comprising:
    an isocyanate-functional methoxy polyethylene glycol combined with at least one multi-functional isocyanate; and
    at least one diamine,
    wherein the isocyanate-functional methoxy polyethylene glycol includes degradable linkages and has pendant polyalkylene oxide groups, and
    wherein the biocompatible surgical adhesive further comprises an enzyme which increases the degradation rate of the degradable linkages.

2. The biocompatible surgical adhesive as in claim 1, wherein the at least one multi-functional isocyanate is selected from the group consisting of diisocyanates, triisocyanates and combinations thereof.

3. The biocompatible surgical adhesive as in claim 1, wherein the at least one multi-functional isocyanate is a diisocyanate selected from the group consisting of toluene diisocyanate, xylylene diisocyanate, bisphenylene diisocyanate, 4,4'-oxybis(phenyl isocyanate), lysine diisocyanate, 2,4,6-trimethyl-1,3-phenylene diisocyanate, naphthylene diisocyanate, diphenylmethane diisocyanate, trimethylene diisocyanate, tetramethylene diisocyanate, pentamethylene diisocyanate, hexamethylene diisocyanate, ethylethylene diisocyanate, trimethylhexane diisocyanate, heptanemethylene diisocyanate, butane diisocyanate, and combinations thereof.

4. The biocompatible surgical adhesive as in claim 1, wherein the at least one multi-functional isocyanate is a triisocyanate selected from the group consisting of triphenylmethane triisocyanate, tris(isocyanatophenyl) thiophosphate, lysine ester triisocyanate, 1,6,11-undecane triisocyanate, 1,3,6-hexamethylene triisocyanate, 1,8-diisocyanato-4-isocyanatomethyloctane, bicycloheptane triisocyanate, and combinations thereof.

5. The biocompatible surgical adhesive as in claim 1, wherein the diamine is selected from the group consisting of ethylene diamine, hexamethylene diamine, N,N'-bis(3-aminopropyl)-1,2-ethane diamine, N-(3-aminopropyl)-1,3-propane diamine, N-(2-aminoethyl)-1,3 propane diamine, N-(3-aminopropyl)-1,4-butane diamine, N,N'-bis(3-aminopropyl)-1,4-butane diamine, cyclohexane diamine, isomers of cyclohexane diamine, toluene diamine, phenylene diamine, and isophorone diamine.

6. The biocompatible surgical adhesive as in claim 1, wherein the isocyanate-functional methoxy polyethylene glycol combined with the at least one multi-functional isocyanate are present in an amount from about 50% to about 99% by weight of the biocompatible surgical adhesive, and the diamine is present in an amount from about 1% to about 50% by weight of the biocompatible surgical adhesive.

7. The biocompatible surgical adhesive as in claim 1, wherein the isocyanate-functional methoxy polyethylene glycol combined with the at least one multi-functional isocyanate are present in an amount from about 5% to about 45% by weight of the biocompatible surgical adhesive, and the diamine is present in an amount from about 55% to about 95% by weight of the biocompatible surgical adhesive.

8. The biocompatible surgical adhesive as in claim 1, wherein the biocompatible surgical adhesive includes a biologically active agent.

9. The biocompatible surgical adhesive as in claim 1, wherein the biocompatible surgical adhesive includes a medicinal agent.

10. A method for closing a wound comprising:
   applying the biocompatible surgical adhesive of claim 1 to said wound; and
   allowing the biocompatible surgical adhesive to set thereby closing said wound.

11. The method of claim 10, wherein the wound is a surgical incision.

12. A method for filling a void in animal tissue comprising:
   applying the biocompatible surgical adhesive of claim 1 to said void; and
   allowing the biocompatible surgical adhesive to set thereby filling said void.

13. A method for adhering a medical device to a surface of animal tissue comprising the steps of:
   applying the biocompatible surgical adhesive of claim 1 to said device, said surface or both;
   bringing the device, biocompatible surgical adhesive and surface into contact with each other; and
   allowing the biocompatible surgical adhesive to set thereby adhering the device and surface to each other.

14. The method of claim 13 wherein said medical device is an implant.

* * * * *